United States Patent [19]

Meeks et al.

[11] Patent Number: 5,137,604

[45] Date of Patent: Aug. 11, 1992

[54] APPARATUS FOR DRYING BIOLOGICAL SPECIMENS

[75] Inventors: Warren Meeks, Columbia, Md.; Yury Zlobinsky, Massapequa, N.Y.

[73] Assignee: Savant Instruments, Inc., Farmingdale, N.Y.

[21] Appl. No.: 549,447

[22] Filed: Jul. 6, 1990

[51] Int. Cl.⁵ .......................... B01D 1/22; B01D 3/10
[52] U.S. Cl. .................... 202/205; 202/236; 159/6.1; 159/16.1; 159/49; 159/DIG. 16; 203/2; 203/89; 210/781; 422/72; 422/101; 436/177; 494/1; 494/25; 494/26; 494/61
[58] Field of Search ................ 159/6.1, 49, 44, 16.1, 159/DIG. 16; 203/2, 4, 49, 89, 72; 202/205, 238, 236; 494/61, 1, 25, 26; 422/72, 101; 436/177; 210/781, 782

[56] References Cited

U.S. PATENT DOCUMENTS

| | | | |
|---|---|---|---|
| 1,575,061 | 3/1926 | Jones et al. | 494/26 |
| 3,304,990 | 2/1967 | Ontko et al. | 494/61 |
| 3,327,938 | 6/1967 | Stallmann | 494/61 |
| 3,871,574 | 3/1975 | Lucas | 494/61 |
| 3,977,935 | 8/1976 | Kowarski | 159/DIG. 16 |
| 4,226,669 | 10/1980 | Vilardi | 159/44 |
| 4,254,943 | 3/1981 | Bjorkman | 202/205 |
| 4,613,412 | 9/1986 | MacDermid | 202/205 |
| 4,857,811 | 8/1989 | Barrett et al. | 494/26 |
| 4,913,771 | 4/1990 | McIntyre | 203/2 |
| 4,929,312 | 5/1990 | Westcott | 203/2 |

Primary Examiner—Wilbur Bascomb, Jr.
Attorney, Agent, or Firm—Morrison Law Firm

[57] ABSTRACT

A solvent-containing biological material specimen is dried in a vacuum chamber with solvent evolving during the drying cycle being condensed in a refrigerated cold trap. During the drying cycle, communication of the drying chamber with the vacuum pump with which the chamber is evacuated, selectively is established or interdicted in response to raising or lowering of the vacuum condition in the chamber with respect to an initially set predetermined vacuum condition. Evolving of solvent from the specimen proceeds during interdiction by way of "cryopumping" due to the differential in pressure between the chamber and the refrigerated trap. Thus maximized solvent recovery in the trap is achieved, and carry over of solvent to the vacuum pump wherein its presence would be contaminating of the pump oil is for practical purpose eliminated. Selective establishment and interdiction of chamber/pump communication provides a controlled vacuum drying operation and lessens "bumping" or foaming of certain highly volatile solvents and volatile biological material as well which if occurring, can cause defects or altered character in the specimen. A unique arrangement of a pair of two-way valves is employed to effect and maintain vacuum control as well as control bleeding of a gas to the chamber and pump at the end of the drying cycle.

8 Claims, 2 Drawing Sheets

FIG_1

APPARATUS FOR DRYING BIOLOGICAL SPECIMENS

BACKGROUND OF THE INVENTION

The present invention relates to drying of biological specimens and refers more particularly to improved method and apparatus by which such drying can be carried out.

In certain laboratory procedures, it is required to separate and concentrate biological material from a solvent-containing specimen, i.e., dry the specimen in preparation for study of the dried specimen material by amino acid analysis, gas chromatography, mass spectroscopy and like. This can be done, e.g., with the Savant Instruments, Inc. Automated SPEEDVAC Systems A160 or A290, which apparatus includes a vacuum centrifuge of the type disclosed in commonly owned U.S. Pat. No. 4,226,669, a vacuum pump for imposing a vacuum on the interior of a drying chamber, i.e., the centrifuge, a refrigerated trap to which solvent vapors evolving in the drying cycle pass for condensing of the same, a microprocessor for controlling the drying apparatus, and conduit tubing as well as a pair of control valves for establishing of blocking communication or conduit flow courses in the systems for various reasons attending the drying operation and cycle.

Both these systems use a three-way drying chamber vacuum control valve disposed in the conduit connecting the drying chamber with the pump and located proximal or adjacent the drying chamber. This three-way valve is a normally open type which when open connects the chamber with ambient atmosphere or an inert gas source. When closed, the valve connects the chamber with the condensate trap located downstream a distance of the chamber. These systems also use a two-way pump bleeder valve adjacent the vacuum pump and on the upstream side of the pump which valve also is a normally open type connected to the conduit leg leading to the pump and cold trap, and when closed, disconnecting the pump and condensation trap from the atmosphere.

With these systems, the vacuum pump during drying cycle is always connected to the drying chamber so that any solvent vapor escaping condensation in the trap can pass therefrom and eventually into the vacuum pump. The solvent contaminates the oil in the pump which necessitates frequent oil change and it also can cause corrosion of pump internal structure. Further, the vacuum pumps in these systems generally will operate at a given constant vacuum level which can be one below that at which certain highly volatile solvents can "bump" from the specimen and carry biological material away from the specimen—a result to be avoided since valuable specimen material constituents can be lost to the detriment of the eventual analysis to which the dried specimen is to be subjected.

OBJECTS AND SUMMARY OF THE INVENTION

Accordingly it is an object of the invention to provide apparatus and method for separating and concentrating biological material from solvents in which such material is contained which overcomes the drawbacks of the prior art.

Another object is to provide specimen separation and concentration apparatus and method that allows application of controlled levels of vacuum in a drying chamber which prevents "bumping" of highly volatile solvents from the specimen sample during drying, and which ability to dry at controlled vacuum levels not as low as inherent in the prior systems, also prevents loss of volatile specimen material itself during thereby preventing carry off of biological material from the sample and loss as a discharge product from the vacuum pump.

Still another object is to provide application of controlled vacuum to a specimen drying chamber which allows isolating the drying chamber from pump vacuum draw for extended time during a drying cycle by allowing "cryopumping" of solvent from the drying chamber to a refrigerated condensate trap to proceed, thereby lessening the chance for solvent to carry forth into the vacuum pump wherein its presence is detrimental to both the oil in the pump and the pump internal structure, and especially, in regard to the latter since, many solvents used in laboratory specimen analysis procedures are corrosive to the pump material. Such solvents can include organic acids, mineral acids, aqueous or volatile organic solvents etc.

Briefly stated, there is provided method and apparatus for drying a solvent-containing biological material specimen, the specimen being dried in a vacuum chamber with solvent evolving during the drying cycle being condensed in a refrigerated cold trap. During the drying cycle, communication between the chamber and chamber evacuating vacuum pump is interdicted or maintained on a selective basis and with reference to departure of the vacuum condition in the chamber from a certain value either above or below an initially set predetermined chamber condition of vacuum. During the drying cycle, evolution of solvent from the specimen proceeds even when chamber/pump connection is interdicted due to "cryopumping", i.e., because a considerable differential of vapor pressure exists between that of the solvent in the specimen (which commonly will be heated to promote drying) and that present in the condensate trap. This continued and maximized solvent recovery achieved for the most part without need for direct pump vacuum pull, results in practical elimination of solvent carry over to the pump and the oil in the pump. Pump oil use-life lengthening and avoidance of corrosive solvent damage to the pump interior parts are achieved. Control of the connection between the chamber and pump as stated above, allows drying at a controlled vacuum level which in turn, prevents "bumping" or foaming of highly volatile solvents from the specimen during drying as vacuum can be controlled at the level needed to avoid such occurrence as well as loss of volatile biological material too. A specially arranged pair of two-way valves is employed to control vacuum condition during the drying cycle and to bleed the vacuum chamber with a gas at the end of the cycle.

According to a feature of the invention, there is further provided a method for drying a solvent-containing biological material specimen which comprises rapidly rotating a holder having an opening at one end in which the specimen is confined and with the holder being disposed in a chamber, about a fixed vertical axis to subject the specimen to a centrifugal force holding the biological material remote from the holder one end. The chamber is evacuated by connecting it to an operating vacuum pump so that vacuum pull from the pump draws solvent from the specimen and outwardly of the chamber, with the solvent withdrawn being passed through a refrigerated condensation trap to condense solvent vapors therein. The connection between the chamber and pump is interdicted at a location downstream of the refrigeration trap when the condition of vacuum in the chamber reaches a predetermined level. The vacuum condition in the chamber is continuously monitored and the chamber is reconnected to the pump whenever the condition of vacuum lowers a certain amount below said predetermined condition of vacuum and again interdicted whenever the condition raises a like certain amount above said predetermined condition. At the end of a predetermined specimen drying time, a flow of gas is admitted to said chamber, the gas flow emanating from an admission location disposed upstream of the interdiction location.

According to another feature of the invention, there is provided apparatus for drying a solvent-containing biological material specimen, said specimen being confined in an open top specimen holder, the apparatus comprising a housing enclosing space defining a drying chamber, a support in said chamber for receiving said specimen holder with the support being such that during operation, the specimen holder will incline or be held inclined relative to a horizontal at an angle of less than 45 degrees, e.g., at about 35 degrees, means are provided for rotating said support about a fixed vertical axis so the specimen in the holder is subjected to centrifugal force whereby the biological material is held remote from the holder open top. A vacuum pump is provided and conduit means communicatively connects the pump and drying chamber for evacuating the chamber to a predetermined condition of vacuum, solvent evaporating from the specimen when said specimen is subjected to a vacuum condition. A refrigerated condensation trap is interposed in the conduit means downstream but proximal said chamber and solvent evaporating from the chamber and outflowing therefrom is condensed in said trap. Two-position power operated valve means is interposed in the conduit means downstream of the trap and has a conduit means non-blocking position whereby connection of the chamber with the pump is unblocked, and a conduit blocking position for blocking the chamber/pump connection. A branch conduit is provided and another two-position power operated valve means. The branch conduit extends between a connection thereof with the conduit means at a location upstream of the first valve means location and the said other valve means, with such other valve means having an open position in which it connects said branch conduit with a gas source such as ambient air or a source of nitrogen, and a closed position in which branch conduit communication with the gas source is blocked. A control means is connected with each valve means for controlling positioning thereof during a specimen drying cycle. The first-mentioned valve means can be selectively positioned in conduit non-blocking position whenever the vacuum condition in the chamber lowers a certain amount below said predetermined condition, and in conduit means blocking position whenever the vacuum condition raises a like certain amount above said predetermined condition, said control means positioning said other two-position valve means in closed position during the drying cycle.

According to a still further feature of the invention, there is still further provided in apparatus for drying a solvent-containing biological material specimen confined in an open top holder which apparatus comprises a housing enclosing space defining a drying chamber, a support in the chamber receiving the specimen holder with the specimen holder inclined relative to a horizontal datum such that the holder open top is positioned above a holder opposite end, means for rotating said support about a fixed vertical axis so that a specimen in said holder is subjected to centrifugal force whereby the biological material of the specimen is held remote from the holder open top, a vacuum pump, conduit means communicatively connecting said pump with said chamber, said pump when operated pulling vacuum on the chamber for evacuating it to a predetermined condition of vacuum, solvent evaporating from the specimen when the specimen is subjected to a vacuum condition, and a refrigerated condensation tank interposed in the conduit means downstream of but proximal said chamber, solvent evaporating from the specimen and outflowing the chamber being condensed in said trap, the combination of first and second valve means a first of such valve means being disposed downstream of the trap, first valve means connected in said conduit means and operable to pass or block communication of said pump with said trap, the second valve means connected to said conduit means at a location upstream of the first valve means and operable to admit or block flow of a gas from a gas source to said chamber via said conduit means at said upstream location.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
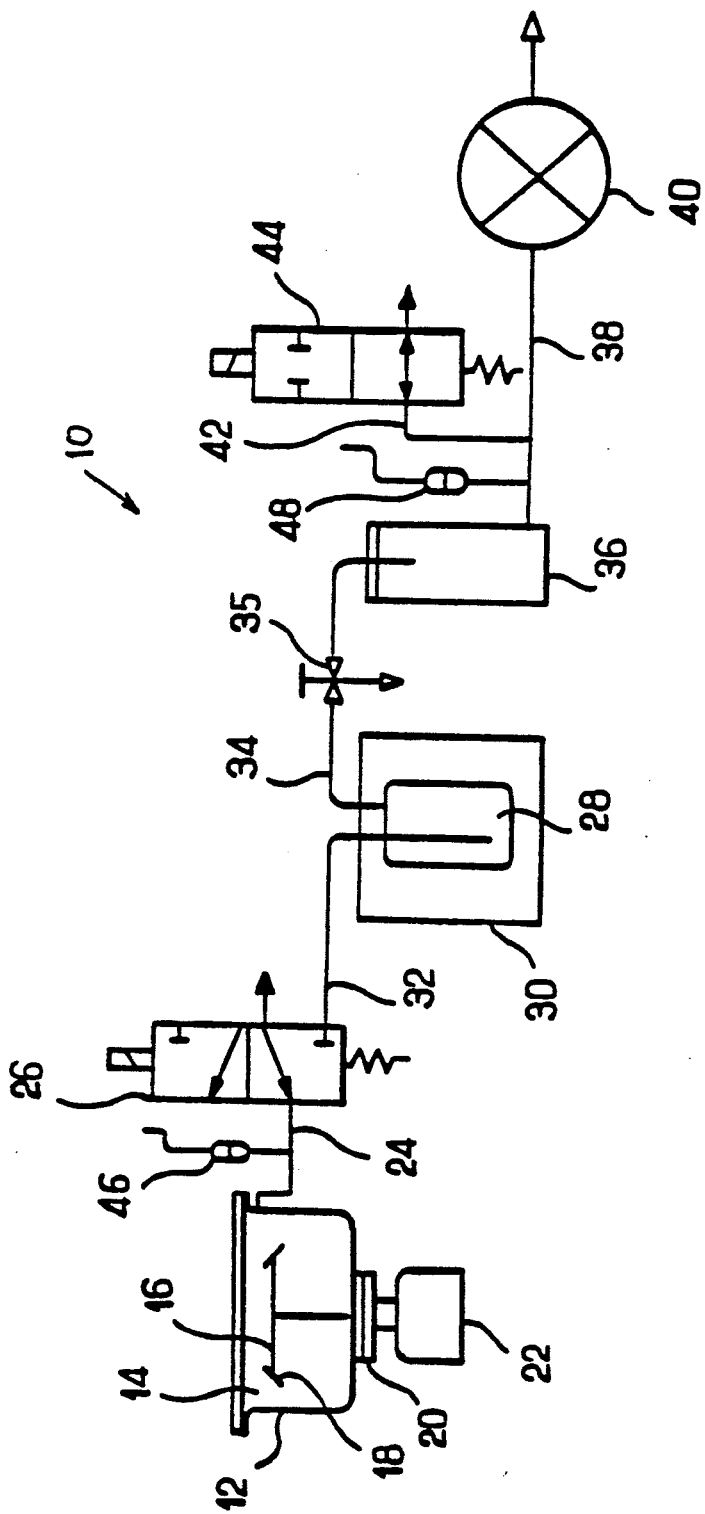
FIG. 1 is a schematic depiction of a prior art vacuum drying system.

Referring to the prior art system 10 shown in FIG. 1, such system represents that designated by the Assignee herein as its Automated SPEEDVAC Systems A160 and A290. System 10 includes a vacuum concentrator 12 of, e.g., the type disclosed in the earlier-referred to '669 patent, the concentrator enclosing a space defining a drying chamber 14 and in which is carried a support 16 for reception of one or a plurality of specimen holders 18.

The holders in which a solvents-containing biological material is disposed, generally will be received in support 16 such that they are inclined to hold the open top thereof radially inwardly of the holder other end and a distance above said other end so that when support 16 is rotated about a fixed vertical axis, centrifugal force will impel heavier biological material in the holder toward said other end, and that force also acting on the solvent inhibits, when vacuum is imposed on the chamber space, "bumping" or foaming in the solvent, particularly highly volatile solvents, thereby to prevent unwanted carrying off of biological material from the specimen and ultimate loss of same (as well as solvent) out of the system via pump discharge. The inclination of the holders during rotation it is understood will be at an angle of less than 45 degrees to the horizontal, the support or rotors used with the SPEEDVAC Systems being designed to thus receive and support the specimen holders.

Support 16 is rotated by motor 22 via magnetic coupling drive 20 in the manner described in the '669 patent.

Vacuum chamber 14 is connected by conduit leg 24 to a three-way poppet or spool valve 26 which valve in turn is connected to a glass insert trap 28 received in refrigerated trap housing 30, this connection being via conduit leg 32. Conduit leg 34 connects glass insert trap 28 with a chemical filter 36, a three-way, manually operated cock 35 being located in leg 34 and used when it is desired to clean out the cold trap. The chemical filter 36 is connected to vacuum pump 40 via conduit leg 38, there being a branch conduit 42 off conduit leg 38 for connecting leg 38 via two-way bleeder poppet valve 44 to atmosphere. Sensors 46, 48 are provided for sensing vacuum levels in the chamber 14 and at the vacuum pump 40, respectively.

When system 10 operates during a drying cycle, normally open poppet valves 26 and 44 are energized-this will occur only some time after the support 16 is started rotating and reaches a speed of about 1000 R.P.M. In the case of valve 26, it will shift from connecting the chamber 14 to atmosphere or other gas source position to a position wherein the chamber is connected via conduit legs 24 and 32 to the vacuum pull of pump 40. In time, a condition of vacuum will build up in the chamber to a maximum value dependent on the pump capacity. In other words, there will be no way of controlling the chamber vacuum to a particular desired predetermined level. It will simply reach a stated level and remain so during the drying.

The drying operation will proceed and solvent, exposed to the vacuum condition of the chamber, will evolve from the specimen and pass out of the chamber and into the cold glass trap where it will condense. Cold trap 28 remains under the vacuum pull influence of the pump so any solvent which does not condense, can be drawn right through the system and into the pump where its presence shortens materially the effective use life of the oil in the pump. Also this solvent in the case of particularly corrosive type solvents, attacks and in time, corrodes pump internal structure requiring repair or discard of the pump.

As was noted above, system 10 does not allow for controlling vacuum in the chamber 14. There is no way to isolate the system forward of the pump and sustain vacuum in chamber 14. And since this vacuum can build up quickly to values at which highly volatile solvents flash from the specimen, and volatile biological specimen material can flash as well, the solvent and/or biological material will be drawn to the pump and lost. Avoidance of pump oil contamination with solvent, avoidance of loss of solvent, avoidance of loss of volatile biological material, and ability to control vacuum in the chamber 14 to desired levels is possible though with the present invention and as shall be detailed next.

Figure 2:
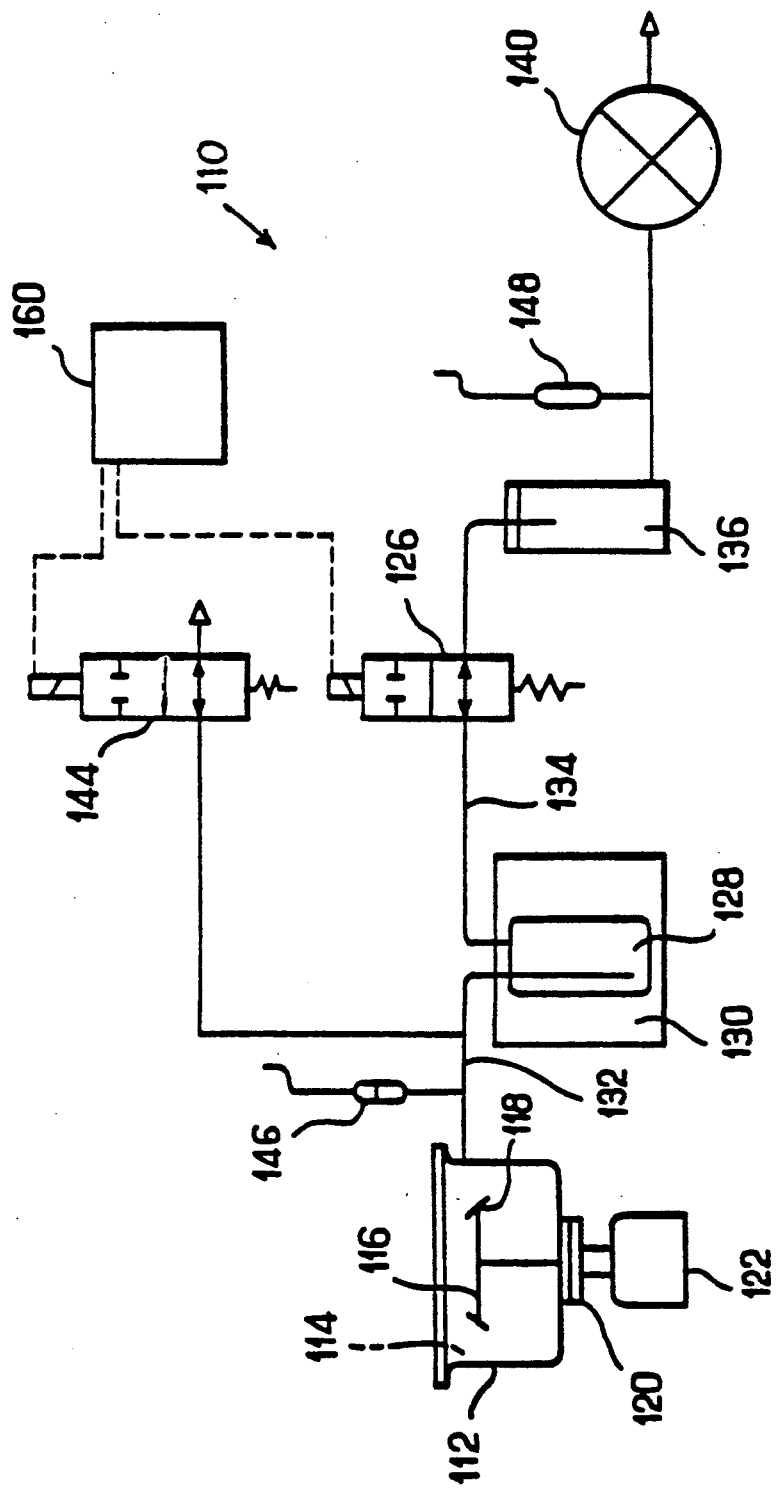
FIG. 2 is a schematic depiction of the vacuum drying system or apparatus provided in accordance with the invention and with which the controlled vacuum drying method of the invention can be carried out.

With reference to FIG. 2, it is to be noted that parts common with those of FIG. 1 bear the same reference numerals increased by 100. A principal difference of system 110 with that of FIG. 1 is the location and functioning of the vacuum control valve 126 and bleeder valve 144. Poppet valve 126 is located a distance downstream of the refrigerated cold trap 128. Thus, this normally open valve when closed during the course of the drying cycle isolates, the system upstream of the valve from the vacuum draw effect of the vacuum pump 140.

With normally open bleeder poppet valve 144 also closed, the system section including the cold trap 128, conduit leg 132 and the chamber 114 constitutes a "cryopumping" route for solvent evolving from the specimen to be caused to flow along and enter and condense in the cold trap.

Solvent flow occurs by reason of the difference of vapor pressure between the solvent in the specimen and that in the cold trap. The solvent in the specimen is heated as heat application to the specimen in the chamber is a common practice employed to accelerate drying, and the cold trap is maintained at about minus 40 degrees C. or lower, vapor pressures at such temperature being very low.

By isolating the system upstream of the vacuum control valve 126, solvent recovery is enhanced since it cannot flow beyond the trap 128 as vacuum draw effect of the pump is barred upstream of valve 126. Further and more importantly, any uncondensed solvent flow to the pump and hence, oil contaminating presence thereof in the pump is for all practical purpose eliminated as is any corrosive effect it could have on the pump itself. This also optimizes solvent recovery.

Isolation of the upstream section of the system requires in addition to the utilization and arrangement of pumps 126, 144, maximized joint and tube tightness in the system conduit legs and the joinder thereof to the components with which used to insure no bleed-in leakage of atmospheric air to the system will take place during drying.

When a specimen is to be dried, it will be placed in chamber 114 and support 116 will be stated to rotate. During initial support speed up, valve 126 will be closed and valve 144 can be either open or closed. When the support reaches about 1000 R.P.M. and with vacuum pump 140 operating, bleeder valve 144 (which is connected at one side with conduit leg 132 at a location upstream of the cold trap 128 via conduit length 158) will be closed, and vacuum valve 126 will be opened so that vacuum draw of the pump will start to draw vacuum on the chamber 114. The valves 126, 144, are electrical solenoid operated poppet valves and are controlled in their respective drying cycle positionings by means of control unit 160, said unit being a programmable microprocessor. On loss of electrical power, both valves will move to open position.

With regard to initial evacuation of the drying chamber, it will be understood that the present invention prescribes this be achieved in a precise and controlled manner involving modulating the opening and closing of valve 126 repeatedly during the vacuum drawdown from atmospheric pressure to an initial desired predetermined condition of vacuum. It is this smooth, initial downpressuring of the drying chamber in sequential, even stepping which mitigates the tendency of volatile solvent and biological specimen material to flash precipitously and thus be lost from the system. The control can, for example, occur by initiating open position of valve 126 for about 1.1 seconds followed by closing for 5. Then opening valve 126 for 1.1 seconds squared followed by closing for 5, opening for 1.1 seconds cubed followed by closing for 5 seconds and so on in steps of ever increasing opening time followed by 5 second closings and until the initial predetermined vacuum is reached at which point, "cryopumping" interdiction as explained earlier will ensue.

After a stated period of time of "cryopumping" during which the negative pressure in the chamber has been lowered to a predetermined condition of vacuum, the control unit will signal the valve 126 to close, isolating the upstream part of the system. Solvent evolution from the specimen and condensation of the solvent in the cold trap as noted above will take place. In time, the vacuum condition will lower (i.e., the absolute pressure in the chamber will increase) a certain amount from the predetermined condition of vacuum and this will be sensed by sensor 146 which will signal the control unit 160 such fact and the control unit in turn will operate to open valve 126 to terminate interdiction of the connection between the chamber and the pump. Pump operation will then cause the condition of vacuum to increase in the chamber and keep up the draw until the absolute pressure lowers a like certain amount below that at the predetermined condition of vacuum, and when that is reached, valve 126 once again will be closed. By way of example, the predetermined condition of vacuum could be about 10000 microns and the increase or decrease of vacuum departure therefrom in a range of about 5% to about 20% from that value before the valve 126 is operated in either closed or open position. In a typical drying cycle, "cryopumping" will be employed about 55 total minutes, whereas, direct pump draw will take place for about 5 minutes.

By utilizing this procedure of closing the vacuum valve to take advantage of "cryopumping" of solvent from the specimen to the cold trap instead of using a steady state draw on the chamber with the pump, the advantages enumerated before are achieved. Further, vacuum in the chamber can be controlled at any ones of numbers of desired levels so as to lessen the problem of flashing volatile biological material during the drying process.

At the end of the drying cycle, valve 126 will be closed and valve 144 opened to admit a bleed gas flow into the chamber 114. After equalization of pressure in the system, valve 144 can be closed. Either air or an inert gas such as nitrogen can be used for the bleed, from a gas source located at the other side of valve 144, e.g., atmospheric air present and accessing the valve as at 159. If a nitrogen bleed is used, it will be employed in controlled amount for only a short duration to equalize pressure in the chamber relative to that exerted on the chamber top by atmosphere and valve 144 will then close to conserve the nitrogen gas source.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Apparatus for drying a solvent-containing biological material specimen, said specimen being confined in an open-top specimen holder, said apparatus comprising, a housing enclosing space defining a drying chamber,
   a support in said chamber for receiving said specimen holder,
   means for rotating said support about a fixed vertical axis so that a specimen in the holder is subjected to centrifugal force whereby biological material therein is held remote from the holder open top,
   a vacuum pump,
   conduit means for communicatively connecting said vacuum pump with said drying chamber, said pump when operated pulling vacuum on said drying chamber for evacuating it to a predetermined condition of vacuum, solvent evaporating from the specimen when said specimen is subjected to vacuum condition,
   a refrigerated condensation trap interposed in said conduit means downstream of said chamber, solvent evaporating from the specimen and outflowing the chamber being condensed in said trap,
   two-position power operated valve means interposed in said conduit means intervening said trap and the pump, said valve means having a conduit means non-blocking position whereby communication of said chamber with said pump is unblocked, and a conduit means blocking position whereby communication of said chamber with the pump is interdicted,
   another two-position power operated valve means, said other valve means being connected by a conduit length with said conduit means at a location upstream of the trap, said other valve means having an open position in which it communicates said conduit length with a gas source, and a closed position in which it blocks communication of said conduit length with said gas source, and
   control means, said control means being connected with each said valve means for controlling the positioning thereof whereby during a specimen drying cycle, the first-mentioned valve means selectively can be positioned in conduit non-blocking position whenever the condition of vacuum in said drying chamber lowers a certain amount below said predetermined condition thereof and in a conduit means blocking position whenever the condition of vacuum in said drying chamber raises a like certain amount above said predetermined condition, said control means being operable to maintain said other valve means closed during the specimen drying cycle so that with the first-mentioned valve means in blocking position solvent due to a vapor pressure differential existing between solvent in the drying chamber and in said trap, continues to evolve and pass from the drying chamber to the trap, said control means being operable further to open said other two-position valve means at the end of a drying cycle.

2. The apparatus of claim 1 in which the respective valve means position in their respective conduit means non-blocking and open positions in the absence of application of operating power thereto.

3. The apparatus of claim 2 in which both said two-position valve means are normally open valves.

4. The apparatus of claim 3 in which said valve means comprises poppet valves.

5. The apparatus of claim 4 in which said valve means comprises electrical solenoid operated valves.

6. In apparatus for drying a solvent containing biological specimen, said specimen being confined in an open-top specimen holder, which apparatus comprises, a housing enclosing space defining a drying chamber,
   a support in said chamber for receiving said specimen holder
   means for rotating said support about a fixed axis so that a specimen in said holder is subjected to centrifugal force whereby the biological material of the specimen is held remote from the holder open top,
   a vacuum pump, conduit means for communicatively connecting said vacuum pump with said drying chamber, said pump when operated pulling vacuum on said drying chamber for evacuating it to a predetermined condition of vacuum, solvent evaporating from the specimen when said specimen is subjected to vacuum condition, and a refrigerated condensation trap interposed in said conduit means downstream of said chamber, solvent evaporating from the specimen and outflowing the chamber being condensed in said trap, the combination of first and second two-position valves, a first of said valves being disposed in the conduit means downstream of the trap and operable to allow or block communication of said pump with said trap, the second valve being connected to said conduit means at a location upstream of the first valve and operable to admit or block flow of a gas from a gas source to said drying chamber via said conduit means at said upstream location.

7. The apparatus of claim 6 in which each valve is a power-operated device and is normally open in absence of power application thereto.

8. In apparatus for drying a solvent-containing biological material specimen, a housing enclosing space defining a drying chamber in which the specimen is received for drying, a vacuum pump, conduit means for communicatively connecting the drying chamber space with the vacuum pump, said pump being operable to evacuate the drying chamber space to a predetermined condition of vacuum so that solvent is caused to evaporate from the specimen by the influence of said vacuum condition, a refrigerated cold trap interposed in the conduit means downstream of the drying chamber into which the solvent evaporating from the specimen can flow and be condensed, a flow control element disposed in said conduit means at a location intervening the cold trap and the vacuum pump, the flow control element being positionable to have flow passing and flow blocking orientations, and means for orienting the flow control element to flow blocking position it whenever the vacuum condition in said drying chamber is at or an amount above said predetermined condition, and to orient the flow control element to flow passing position it whenever the vacuum condition in the drying chamber is at least a like amount below said predetermined condition.

* * * * *